United States Patent
d'Lima et al.

(10) Patent No.: US 9,914,911 B2
(45) Date of Patent: Mar. 13, 2018

(54) METHODS OF REPROGRAMMING CHONDROCYTES

(71) Applicant: Scripps Health, San Diego, CA (US)

(72) Inventors: Darryl D. d'Lima, San Diego, CA (US); Tsaiwei Olee, San Diego, CA (US); Clifford W. Colwell, San Diego, CA (US)

(73) Assignee: SCRIPPS HEALTH, San Diego, CA (US)

( * ) Notice: Subject to any disclaimer, the term of this patent is extended or adjusted under 35 U.S.C. 154(b) by 0 days.

(21) Appl. No.: 14/438,581

(22) PCT Filed: Oct. 29, 2013

(86) PCT No.: PCT/US2013/067350
§ 371 (c)(1),
(2) Date: Apr. 24, 2015

(87) PCT Pub. No.: WO2014/070797
PCT Pub. Date: May 8, 2014

(65) Prior Publication Data
US 2015/0275181 A1    Oct. 1, 2015

Related U.S. Application Data

(60) Provisional application No. 61/719,901, filed on Oct. 29, 2012.

(51) Int. Cl.
*C12N 5/00* (2006.01)
*C12N 15/00* (2006.01)
(Continued)

(52) U.S. Cl.
CPC .......... *C12N 5/0696* (2013.01); *A61K 35/32* (2013.01); *A61K 35/545* (2013.01);
(Continued)

(58) Field of Classification Search
USPC .................................................. 435/325, 455
See application file for complete search history.

(56) References Cited

U.S. PATENT DOCUMENTS

| 5,399,347 A | 3/1995 | Trentham et al. |
| 5,645,851 A | 7/1997 | Moore |

(Continued)

FOREIGN PATENT DOCUMENTS

| CN | 101810855 A | 8/2010 |
| CN | 101934092 A | 1/2011 |

(Continued)

OTHER PUBLICATIONS

Zahabi (Stem Cells and Develop., 2012, vol. 21, No. 12, p. 2262-2272).*

(Continued)

*Primary Examiner* — Michael C Wilson
(74) *Attorney, Agent, or Firm* — Wilson Sonsini Goodrich & Rosati (57) ABSTRACT

Disclosed herein are methods of producing induced pluripotent stem cells from chondrocytes, and further, methods of producing chondrocytes from said induced pluripotent stem cells. The invention further provides methods of regenerating cartilaginous tissue.

8 Claims, 4 Drawing Sheets

(51) Int. Cl.
    *C12N 5/074* (2010.01)
    *A61K 35/32* (2015.01)
    *A61K 35/545* (2015.01)

(52) U.S. Cl.
    CPC .... *C12N 2501/15* (2013.01); *C12N 2501/155* (2013.01); *C12N 2501/385* (2013.01); *C12N 2501/602* (2013.01); *C12N 2501/603* (2013.01); *C12N 2501/604* (2013.01); *C12N 2501/606* (2013.01); *C12N 2506/13* (2013.01); *C12N 2510/00* (2013.01); *C12N 2513/00* (2013.01); *C12N 2533/54* (2013.01)

(56) References Cited

U.S. PATENT DOCUMENTS

| | | |
|---|---|---|
| 5,843,780 A | 12/1998 | Thomson |
| 6,025,327 A | 2/2000 | Alkayali |
| 6,200,806 B1 | 3/2001 | Thomson |
| 6,323,319 B1 | 11/2001 | Alkayali |
| 6,511,958 B1 | 1/2003 | Atkinson et al. |
| 6,780,841 B2 | 8/2004 | Ishaq |
| 2002/0090391 A1 | 7/2002 | Geistlich et al. |
| 2003/0026786 A1 | 2/2003 | Pittenger et al. |
| 2003/0091652 A1 | 5/2003 | Ishaq |
| 2003/0152556 A1 | 8/2003 | Lai et al. |
| 2004/0213852 A1 | 10/2004 | Severus et al. |
| 2006/0189840 A1 | 8/2006 | Walsh et al. |
| 2006/0239980 A1 | 10/2006 | Bernad et al. |
| 2007/0293427 A1 | 12/2007 | Vouland et al. |
| 2010/0047212 A1* | 2/2010 | Farinas Gomez ..... A61K 38/57 424/93.7 |
| 2011/0064810 A1 | 3/2011 | Ghanavi |
| 2011/0256109 A1 | 10/2011 | Noble et al. |
| 2012/0034271 A1 | 2/2012 | Shu |
| 2012/0100103 A1 | 4/2012 | Park et al. |
| 2015/0259648 A1 | 9/2015 | D'Lima et al. |
| 2015/0283303 A1 | 10/2015 | D'Lima et al. |
| 2016/0040123 A1* | 2/2016 | Kanemura ........... C12N 5/0081 435/375 |

FOREIGN PATENT DOCUMENTS

| | | |
|---|---|---|
| EP | 1312383 A2 | 5/2003 |
| JP | 2011015662 A | 1/2011 |
| KR | 20120046430 A | 5/2012 |
| WO | WO-2011065661 A2 | 6/2011 |
| WO | WO-2011066403 A1 | 6/2011 |
| WO | WO-2011091475 A1 | 8/2011 |
| WO | WO-2011123572 A1 | 10/2011 |
| WO | WO-2011124894 A1 | 10/2011 |
| WO | WO-2012013969 A1 | 2/2012 |
| WO | WO-2012126824 A1 | 9/2012 |
| WO | WO-2014052912 A1 | 4/2014 |
| WO | WO-2014070796 A1 | 5/2014 |
| WO | WO-2014070797 A1 | 5/2014 |

OTHER PUBLICATIONS

Feng (Cell Stem Cell, Apr. 3, 2009, vol. 4, p. 301-312).*
Wei (European Cells and Materials, 2012, vol. 23, p. 1-12).*
Elshal (Naunyn-Schmiedeberg's Arch Pharmacol, 2015, vol. 388, p. 1293-1304).*
Nyberg (Cancer Res., May 15, 2005, vol. 65, No. 10, p. 3967-3979).*
Dawson (Sci Jul. 9, 1999, vol. 285, p. 245).*
Quan (Calcif Tissue Int, 2005, vol. 76, p. 146-153).*
Kim et al. Generation of human induced pluripotent stem cells from osteoarthritis patient-derived synovial cells. Arthritis Rheum 63(10):3010-3021 (2011).
Raghunath et al. Advancing cartilage tissue engineering: the application of stem cell technology. Curr Opin Biotechnol 16(5):503-509 (2005).
Crowley et al. Safety and efficacy of undenatured type II collagen in the treatment of osteoarthritis of the knee: a clinical trial. Int J Med Sci 6(6):312-321 (2009).
Liu et al. One-step derivation of mesenchymal stem cell (MSC)-like cells from human pluripotent stem cells on a fibrillar collagen coating. PLos One 7(3):e33225 (2012).
PCT/US2013/062437 International Preliminary Report on Patentability dated Apr. 9, 2015.
PCT/US2013/062437 International Search Report and Written Opinion dated Jan. 14, 2014.
PCT/US2013/067349 International Preliminary Report on Patentability dated May 14, 2015.
PCT/US2013-067349 International Search Report and Written Opinion dated Dec. 20, 2013.
PCT/US2013/067350 International Preliminary Report on Patentability dated May 14, 2015.
PCT/US2013/067350 International Search Report and Written Opinion dated Jan. 28, 2014.
Thomson et al. Embryonic stem cell lines derived from human blastocysts. Science 282(5391):1145-1147 (1998).
Thomson et al. Isolation of a primate embryonic stem cell line. PNAS USA 92(17):7844-7848 (1995).
Thomson et al. Primate embryonic stem cells. Curr Top Dev Biol 38:133-165 (1998).
Wei et al. Chondrogenic differentiation of induced pluripotent stem cells from osteoarthritic chondrocytes in alginate matrix. Eur Cell Mater 23:1-12 (2012).
Jihong et al. A potential use of collagen-hyaluronan-chondroitin sulfate tri-copolymer scaffold for cartilage tissue engineering. Zhongguo Xiu Fu Chong Jian Wai Ke Za Zhi 20(2):130-133 Database Accession No. NLM16529321 (1 pg.) (2006).
Ko et al. Type II collagen-chondroitin sulfate-hyaluronan scaffold cross-linked by genipin for cartilage tissue engineering. J Biosci Bioeng 107(2):177-182 (2009).
Boeuf et al. Subtractive gene expression profiling of articular cartilage and mesenchymal stem cells: serpins as cartilage-relevant differentiation markers. Osteoarthritis and Cartilage 16(1):48-60 (2008).
Pfander et al. Pigment epithelium derived factor—the product of the EPC-1 gene—is expressed by articular chondrocytes and up regulated in osteoarthritis. Ann Rheum Dis 65(7):965-967 (2006).
Even-Ram et al. Matrix control of stem cell fate. Cell 126(4):645-647 (2006).
Oldershaw et al. Directed differentiation of human embryonic stem cells toward chondrocytes. Nat Biotechnol 28(11):1187-1194 (2010).
Tse et al. Stiffness gradients mimicking in vivo tissue variation regulate mesenchymal stem cell fate. PLOS ONE 6(1):e15978 (2011).
Barberi et al. Derivation of multipotent mesenchymal precursors from human embryonic stem cells. PLoS Med 2(6):e161 (2005).
Davidenko et al. Collagen-hyaluronic acid scaffolds for adipose tissue engineering. Acta Biomater 6(10):3957-3968 (2010).
Gong et al. Direct and progressive differentiation of human embryonic stem cells into the chondrogenic lineage. J Cell Physiol 224(3):664-671 (2010).
Ko et al. Genipin cross-linking of type II collagen-chondroitin sulfate-hyaluronan scaffold for articular cartilage therapy. J Med Biol Eng 27(1):7-14 (2007).
Nagler-Anderson et al. Suppression of type II collagen-induced arthritis by intragastric administration of soluble type II collagen. PNAS USA 83(19):7443-7746 (1986).
Peal et al. Therapeutic efficacy and safety of undenatured type-II collagen (UC-II) alone or in combination with (-)-hydroxycitric acid and chromemate in arthritic dogs. J Vet Phrmacol Ther 30(3):275-278 (2007).
Schauss et al. Acute and subchronic oral toxicity studies in rats of a hydrolyzed chicken sternal cartilage preparation. Food Chem Toxicol 45(2):315-321 (2007).
U.S. Appl. No. 14/438,583 Office Action dated Sep. 30, 2016.
Yang et al. Stage-dependent effect of TGF-beta1 on chondrogenic differentiation of human embryonic stem cells. Stem Cells Dev 18(6):929-940 (2009).

(56) References Cited

OTHER PUBLICATIONS

Calderon et al. Type II collagen-hyaluronan hydrogel—a step towards a scaffold for intervertebral disc tissue engineering. Eur Cell Mater 20:134-148 (2010).

Guo et al. Hydrogels of collagen/chondroitin sulfate/hyaluronan interpenetrating polymer network for cartilage tissue engineering. J Mater Sci Mater Med 23(9):2267-2279 (2012).

Kawasaki et al. Hyaluronic acid enhances proliferation and chondroitin sulfate synthesis in cultured chondrocytes embedded in collagen gels. J Cell Physiol 179(2):142-148 (1999).

Nishimoto et al. Effect of chondroitin sulfate and hyaluronic acid on gene expression in a three-dimensional culture of chondrocytes. J Biosci Bioeng 100(1):123-126 (2005).

Pieper et al. Crosslinked type II collagen matrices: preparation, characterization, and potential for cartilage engineering. Biomaterials 23:3183-3192 (2002).

Sheu et al. Characterization of collagen gel solutions and collagen matrices for cell culture. Biomaterials 22:1713-1719 (2001).

U.S. Appl. No. 14/438,583 Office Action dated Apr. 13, 2017.

Zhang et al. Preparation of collagen—chondroitin sulfate—hyaluronic acid hybrid hydrogel scaffolds and cell compatibility in vitro. Carbohydrate Polymers 84(1):118-125 (2011).

Oh et al. Methods for Expansion of Human Embryonic Stem Cells. Stem Cells 23(5):605-609 (2005).

U.S. Appl. No. 14/431,893 Office Action dated Sep. 26, 2017.

Bian et al. Enhanced MSC Chondrogenesis Following Delivery of TGF-β3 from Alginate Microspheres within Hyaluronic Acid Hydrogels In Vitro and In Vivo. Biomaterials 32(27):6425-6434 (2011).

Takahashi et al. Induction of Pluripotent Stem Cells from Adult Human Fibroblasts by Defined Factors. Cell 131:861-872 (2007).

U.S. Appl. No. 14/431,893 Office Action dated Mar. 22, 2017.

Zheng et al. Chondrogenic differentiation of mesenchymal stem cells induced by collagen-based hydrogel: An in vivo study. J Biomed Mater Res A 93(2):783-792 (2010).

U.S. Appl. No. 14/438,583 Office Action dated Jul. 24, 2017.

\* cited by examiner

METHODS OF REPROGRAMMING CHONDROCYTES

CROSS-REFERENCE

This application is a U.S. National Stage entry of International Application No. PCT/US2013/067350, filed Oct. 29, 2013, which claims the benefit of U.S. application Ser. No. 61/719,901, filed Oct. 29, 2012, all of which are incorporated herein by reference in their entireties.

BACKGROUND OF THE INVENTION

Arthritis and cartilage degeneration are leading causes of disability in both the aging population as well as in younger demographics that engage in increasingly intense physical activity starting at earlier ages.

SUMMARY OF THE INVENTION

Disclosed herein, in some embodiments, is a method of generating a population of pluripotent or multipotent stem cells from a population of chondrocytes, comprising: a) directing expression of one or more of an Oct3/4 polypeptide, a Sox2 polypeptide, a Klf4 polypeptide, and a c-Myc polypeptide in a population of chondrocytes; and b) culturing the chondrocytes in the presence of pigment epithelium-derived factor (PEDF). In some embodiments, the method further comprises introducing into the population of chondrocytes one or more expression vectors for directing expression of the Oct 3/4, Sox2, Klf4, and c-Myc polypeptides. In some embodiments, the one or more expression vectors are retroviral expression vectors, lentiviral expression vectors, adeno-associated viral expression vectors, or adenoviral expression vectors. In some embodiments, the one or more expression vectors are lentiviral expression vectors. In some embodiments, the one or more expression vectors comprise a selection marker. In some embodiments, the pluripotent or multipotent stem cells express two or more genes selected from the group consisting of Oct4, Rex-1, SSEA4, Tra1-60 and Tra1-81. In some embodiments, the chondrocytes are from an adult human.

Disclosed herein, in some embodiments, is a method of generating a population of chondrocytes from a population of pluripotent or multipotent stem cells comprising: i) generating a population of pluripotent or multipotent stem cells according to the methods disclosed herein; ii) mechanically dissecting the pluripotent or multipotent stem cell colonies in order to produce cell aggregates; iii) culturing the cell aggregates in a tissue culture-treated vessel until confluency in order to produce aggregate-derived cells; iv) passaging the aggregate-derived cells in culture at least once in order to produce chondroprogenitors; and v) placing the chondroprogenitors into three-dimensional culture; wherein the method does not comprise formation of an embryoid body. In some embodiments, the aggregate-derived cells are passaged at least two times in order to produce chondroprogenitors. In some embodiments, the aggregate-derived cells are passaged at least three times in order to produce chondroprogenitors. In some embodiments, the aggregate-derived cells are passaged at least four times in order to produce chondroprogenitors. In some embodiments, the aggregate-derived cells are passaged at least five times in order to produce chondroprogenitors. In some embodiments, the aggregate-derived cells are passaged at least six, seven, or eight times in order to produce chondroprogenitors. In some embodiments, the chondroprogenitors are placed into three-dimensional aggregate culture in the presence of TGF-β3. In some embodiments, the chondroprogenitors are placed into three-dimensional aggregate culture in the presence of BMP2. In some embodiments, the process of producing cell aggregates does not comprise enzymatic digestion of the pluripotent or multipotent stem cells. In some embodiments, culturing the chondroprogenitors in three dimensional culture comprises culturing the cells within a three-dimensional matrix. In some embodiments, the three-dimensional matrix comprises collagen, proteoglycan, fibrin, hyaluronic acid, poly-D-lactide, poly-L-lactide, poly-DL-lactide, polyglycolic acid, polylactic acid, hydroxyapatite, calcium phosphate, aterocollagen, fibrin, alginate, agar and/or gelatin. In some embodiments, the three-dimensional matrix comprises collagen. In some embodiments, the collagen is cross-linked. In some embodiments, the collagen is solubilized. In some embodiments, the three-dimensional matrix comprises proteoglycan. In some embodiments, the tissue culture-treated vessel is plastic. In some embodiments, the tissue culture-treated vessel is polystyrene.

Disclosed herein, in some embodiments, is a population of induced pluripotent stem (iPS) cells, wherein the stem cells are derived from a population of chondrocytes. In some embodiments, the iPS cells were induced from chondrocytes that have been passaged twelve or fewer times after being taken from a live donor. In some embodiments, iPS cells were induced from chondrocytes that have been passaged four or fewer times after being taken from a live donor. In some embodiments, the population of iPS cells retain DNA hypo- and hyper-methylation profiles similar to the chondrocytes from which they are derived. In some embodiments, the iPS cells express two or more genes selected from the group consisting of Oct4, Rex-1, SSEA4, Tra1-60 and Tra1-81. In some embodiments, the iPS cells are generated by a method comprising directing expression of an Oct3/4 polypeptide, a Sox2 polypeptide, and a Klf4 polypeptide in a population of chondrocytes. In some embodiments, directing the expression of Oct 3/4, Sox2, and Klf4, comprises introducing into the chondrocytes one or more expression vectors for expression of the Oct 3/4, Sox2, and Klf4 polypeptides. In some embodiments, the one or more expression vectors are retroviral expression vectors, lentiviral expression vectors, adeno-associated viral expression vectors, or adenoviral expression vectors. In some embodiments, the one or more expression vectors is a lentiviral expression vector. In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic.

Disclosed herein, in some embodiments, is a population of cells, wherein the population of cells has been produced by a process comprising: (i) generating a population of pluripotent or multipotent stem cells from a population of chondrocytes by directing expression of polypeptides in the chondrocytes, wherein the polypeptides comprise one or more of an Oct3/4 polypeptide, a Sox2 polypeptide, a Klf4 polypeptide, and a c-Myc polypeptide; (ii) mechanically dissecting the pluripotent or multipotent stem cell colonies in order to produce cell aggregates; (iii) passaging the cells in culture at least once in order to produce chondroprogenitors; and iv) placing the chondroprogenitors into three-dimensional aggregate culture. In some embodiments, the population of cells is homogeneous. In some embodiments, the population of pluripotent or multipotent stem cells are cultured in the presence of pigment epithelium-derived factor (PEDF) prior to step (ii). In some embodiments, the aggregate-derived cells have been passaged at least two times in order to produce chondroprogenitors. In some embodiments, the aggregate-derived cells are passaged at least three times in order to produce chondroprogenitors. In some embodiments, the aggregate-derived cells are passaged at least four times in order to produce chondroprogenitors. In some embodiments, the aggregate-derived cells are passaged at least five times in order to produce chondroprogenitors. In some embodiments, the aggregate-derived cells are passaged at least six, seven, or eight times in order to produce chondroprogenitors.

Disclosed herein, in some embodiments, is a method of regenerating cartilaginous tissue, comprising transplanting a population of cell, as disclosed herein, to a bone or cartilage defect, wherein new tissue is produced. In some embodiments, the population of cells is transplanted into a bone or cartilage defect in a subject in need thereof. In some embodiments, the new tissue integrates with the tissue of the bone or cartilage defect. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin. In some embodiments, the new tissue does not comprise teratomas, neoplastic cells, evidence of deformation, abnormal architectural features, or other inappropriate cell types. In some embodiments, the method further comprises administering an agent or device to block vascular invasion at the site of the bone or cartilage defect.

Disclosed herein, in some embodiments, is a method of treating a bone or cartilage defect, comprising transplantation of a population of cells, as disclosed herein, to the bone or cartilage defect. In some embodiments, new tissue is produced. In some embodiments, the new tissue integrates with the tissue of the bone or cartilage defect. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin.

Disclosed herein, in some embodiments, is a method of treating a cartilage-related disorder in a subject in need thereof, comprising administering a population of cells as disclosed herein to a site of cartilage injury or defect. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is the use of a population of cells disclosed herein in the manufacture of a medicament for treating a cartilage-related disorder. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a biomaterial and a population of cells as disclosed herein. In some embodiments, the biomaterial is: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof.

Disclosed herein, in some embodiments, is a method of generating a population of cardiomyocytes from a population of pluripotent or multipotent stem cells comprising: i) generating a population of pluripotent or multipotent stem cells according to the method of claim 1; ii) allowing the population of pluripotent or multipotent stem cells to form embryoid bodies; iii) adding BMP4 to the culture medium; iv) adding BMP4, Activin A, and FGF-β for days 1-3 after step iii); v) adding DKK and VEGF for days 3-8 after step iii); and vi) adding DKK, VEGF, and FGF-β for days 8-14 after step iii). In some embodiments, on day 0, about 5 ng/ml of BMP4 is added to the culture medium. In some embodiments, on day 1, about 10 ng/ml of BMP4, about 6 ng/ml of Activin A, and about 5 ng/ml of FGF-beta are added to the culture medium. In some embodiments, on day 3, about 150 ng/ml of DKK and about 5 ng/ml of VEGF are added to the culture medium. In some embodiments, on day 8, about 150 ng/ml of DKK, about 10 ng/ml of VEGF and about 5 ng/ml of FGF-beta are added to the culture medium.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Cartilage is formed in the ear, nose, trachea, joints and intervertebral discs. When cartilage is impaired by trauma (such as damage of articular cartilage), or by aging-related diseases (such as arthrosis deformans), inflammatory diseases (such as rheumatoid arthritis), large-sized cartilage defect after surgery of tumors, and congenital anomaly, daily life is severely impaired such that normal everyday activities such as walking become painful and debilitating.

Disclosed herein, in certain embodiments, are methods of culturing human chondrocytes without obtaining mesenchymal stem cells from multiple bone marrow donors. This method may be used to provide a supply of chondrocytes for use in research, pharmaceutical development, and the therapeutic management cartilage-defect related diseases and disorders. Further disclosed herein, in certain embodiments, are cartilage therapy materials using the produced chondrocytes.

Disclosed herein, in some embodiments, is a method of generating a population of pluripotent or multipotent cells from a population of chondrocytes, comprising: a) directing expression of one or more of Oct3/4, Sox2, Klf4, and c-Myc in a population of chondrocytes; and b) culturing the chondrocytes in the presence of pigment epithelium-derived factor (PEDF), to produce a population of pluripotent or multipotent cells. In some embodiments, the method further comprises introducing into the population of chondrocytes one or more expression vectors for directing expression of the Oct 3/4, Sox2, Klf4, and c-Myc. In some embodiments, the one or more expression vectors are retroviral expression vectors, lentiviral expression vectors, adeno-associated viral expression vectors, or adenoviral expression vectors. In some embodiments, the one or more expression vectors are lentiviral expression vectors. In some embodiments, the one or more expression vectors comprise a selection marker. In some embodiments, the pluripotent or multipotent stem cells express two or more genes selected from the group consisting of Oct4, Rex-1, SSEA4, Tra1-60 and Tra1-81. In some embodiments, the chondrocytes are from an adult human.

Disclosed herein, in some embodiments, is a method of generating a population of chondrocytes from a population of pluripotent or multipotent stem cells comprising: i) generating a population of pluripotent or multipotent stem cells according to the methods disclosed herein; ii) mechanically dissecting the pluripotent or multipotent stem cell colonies, to produce cell aggregates; iii) culturing the cell aggregates in a tissue culture-treated vessel until confluency to produce aggregate-derived cells; iv) passaging the aggregate-derived cells in culture at least once in order to produce chondroprogenitors; and v) culturing the chondroprogenitors in a three-dimensional culture; wherein the method does not comprise formation of an embryoid body. In some embodiments, the aggregate-derived cells are passaged at least two times. In some embodiments, the aggregate-derived cells are passaged at least three times. In some embodiments, the aggregate-derived cells are passaged. In some embodiments, the aggregate-derived cells are passaged at least five times. In some embodiments, the aggregate-derived cells are passaged at least six, seven, or eight times. In some embodiments, the three-dimensional culture comprises TGF-β3. In some embodiments, the three-dimensional culture comprises BMP2. In some embodiments, the process of producing cell aggregates does not comprise enzymatic digestion of the pluripotent or multipotent stem cells. In some embodiments, the three dimensional culture comprises a three-dimensional matrix. In some embodiments, the three-dimensional matrix comprises collagen, proteoglycan, fibrin, hyaluronic acid, poly-D-lactide, poly-L-lactide, poly-DL-lactide, polyglycolic acid, polylactic acid, hydroxyapatite, calcium phosphate, aterocollagen, fibrin, alginate, agar and/or gelatin. In some embodiments, the three-dimensional matrix comprises collagen. In some embodiments, the collagen is cross-linked. In some embodiments, the collagen is solubilized. In some embodiments, the three-dimensional matrix comprises proteoglycan. In some embodiments, the tissue culture-treated vessel is plastic. In some embodiments, the tissue culture-treated vessel is polystyrene.

Disclosed herein, in some embodiments, is a population of induced pluripotent stem (iPS) cells, wherein the iPS cells are derived from a population of chondrocytes. In some embodiments, the population of chondrocytes are passaged twelve or fewer times after being taken from a live donor. In some embodiments, the chondrocytes are passaged four or fewer times after being taken from a live donor. In some embodiments, the population of iPS cells have DNA hypo- and hyper-methylation profiles similar to the chondrocytes from which they are derived. In some embodiments, the iPS cells express two or more genes selected from the group consisting of Oct4, Rex-1, SSEA4, Tra1-60 and Tra1-81. In some embodiments, the iPS cells are generated by a method comprising directing expression of one or more of Oct3/4, Sox2, and Klf4 in a population of chondrocytes. In some embodiments, directing the expression of Oct 3/4, Sox2, and Klf4, comprises introducing into the chondrocytes one or more expression vectors for expression of the Oct 3/4, Sox2, and Klf4 polypeptides. In some embodiments, the one or more expression vectors are retroviral expression vectors, lentiviral expression vectors, adeno-associated viral expression vectors, or adenoviral expression vectors. In some embodiments, the one or more expression vectors is a lentiviral expression vector. In some embodiments, the population of iPS cells is less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic.

Disclosed herein, in some embodiments, is a population of cells produced by a process comprising: (i) generating a population of pluripotent or multipotent cells from a population of chondrocytes by directing expression of Oct3/4, Sox2, Klf4, and c-Myc to produce a population of pluripotent or multipotent cells; (ii) mechanically dissecting the pluripotent or multipotent cell colonies to produce cell aggregates; (iii) passaging the cell aggregates in culture at least once to produce chondroprogenitors; and iv) culturing chondroprogenitors in three-dimensional culture. In some embodiments, the population of cells is homogeneous. In some embodiments, the population of pluripotent or multipotent cells are cultured in the presence of pigment epithelium-derived factor (PEDF) prior to step (ii). In some embodiments, the aggregate-derived cells have been passaged at least two times. In some embodiments, the aggregate-derived cells are passaged at least three times. In some embodiments, the aggregate-derived cells are passaged at least four times. In some embodiments, the aggregate-derived cells are passaged at least five times. In some embodiments, the aggregate-derived cells are passaged at least six, seven, or eight times.

Disclosed herein, in some embodiments, is a method of regenerating cartilaginous tissue, comprising transplanting a population of cells, as produced by the methods disclosed herein, to a bone or cartilage defect, wherein new cartilaginous tissue is produced. In some embodiments, the population of cells is transplanted into a bone or cartilage defect in a subject in need thereof. In some embodiments, the new cartilaginous tissue integrates with the tissue of the bone or cartilage defect. In some embodiments, the new cartilaginous tissue restores the surface of the cartilage or bone. In some embodiments, the new cartilaginous tissue comprises collagen type II. In some embodiments, the new cartilaginous tissue comprises superficial, intermediate, and deep zones characteristic of normal articular cartilage. In some embodiments, the superficial zone of the new cartilaginous tissue comprises lubricin. In some embodiments, the new cartilaginous tissue does not comprise teratomas, neoplastic cells, evidence of deformation, abnormal architectural features, or other inappropriate cell types. In some embodiments, the method further comprises administering an agent or device to block vascular invasion at the site of the bone or cartilage defect.

Disclosed herein, in some embodiments, is a method of treating a bone or cartilage defect, comprising transplantation of a population of cells, produced by the methods disclosed herein, to the bone or cartilage defect. In some embodiments, new cartilaginous tissue is produced. In some embodiments, the new cartilaginous tissue integrates with the tissue of the bone or cartilage defect. In some embodiments, the new cartilaginous tissue restores the surface of the cartilage or bone. In some embodiments, the new cartilaginous tissue comprises collagen type II. In some embodiments, the new cartilaginous tissue comprises superficial, intermediate, and deep zones characteristic of normal articular cartilage. In some embodiments, the superficial zone of the new cartilaginous tissue comprises lubricin.

Disclosed herein, in some embodiments, is a method of treating a cartilage-related disorder in a subject in need thereof, comprising administering a population of cells, as produced by the methods disclosed herein to a site of cartilage injury or defect. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is the use of a population of cells disclosed herein for treating a cartilage-related disorder. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a biomaterial substrate and a population of cells as disclosed herein. In some embodiments, the biomaterial substrate is: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof.

Disclosed herein, in some embodiments, is a method of generating a population of cardiomyocytes from a population of pluripotent or multipotent cells comprising: i) generating a population of pluripotent or multipotent cells according to the methods disclosed herein; ii) allowing the population of pluripotent or multipotent cells to form embryoid bodies in a culture medium; iii) adding BMP4 to the culture medium (day 0); iv) adding BMP4, Activin A, and FGF-β for days 1-3 after step iii); v) adding DKK and VEGF for days 3-8 after step iii); and vi) adding DKK, VEGF, and FGF-β for days 8-14 after step iii). In some embodiments, on day 0, about 5 ng/ml of BMP4 is added to the culture medium. In some embodiments, on day 1, about 10 ng/ml of BMP4, about 6 ng/ml of Activin A, and about 5 ng/ml of FGF-beta are added to the culture medium. In some embodiments, on day 3, about 150 ng/ml of DKK and about 5 ng/ml of VEGF are added to the culture medium. In some embodiments, on day 8, about 150 ng/ml of DKK, about 10 ng/ml of VEGF and about 5 ng/ml of FGF-beta are added to the culture medium.

Generating Induced Pluripotent Stem Cells from Chondrocytes

Disclosed herein are methods and compositions for generating pluripotent or multipotent cells from a population of chondrocytes.

Disclosed herein, in some embodiments, are methods of generating a population of pluripotent or multipotent cells from a population of chondrocytes, comprising: a) directing expression of Oct3/4 polypeptide, a Sox2 polypeptide, a Klf4 polypeptide, and a c-Myc polypeptide in a population of chondrocytes; and b) culturing in the presence of pigment epithelium-derived factor (PEDF). In some embodiments, the method further comprises transforming the population of chondrocytes with one or more expression vectors for expression of the Oct 3/4, Sox2, Klf4, and c-Myc polypeptides. In some embodiments, the one or more expression vectors are each independently selected form: retroviral expression vectors, lentiviral expression vectors, adeno-associated viral expression vectors, and adenoviral expression vectors. In some embodiments, at least one of the one or more expression vectors is a lentiviral expression vector. In some embodiments, at least one of the one or more expression vectors comprises a selection marker. In some embodiments, the pluripotent or multipotent cells express two or more genes selected from the group consisting of Oct4, Rex-1, SSEA4, Tra1-60 and Tra1-81. In some embodiments, the chondrocytes are from an adult human. In some embodiments, the chondrocytes are from a human children or human adolescents.

In some embodiments, disclosed herein is a population of induced pluripotent stem cells, wherein the iPS cells are derived from a population of chondrocytes. In some embodiments, the iPS cells were induced from chondrocytes passaged twelve or fewer times after being taken from a live donor. In some embodiments, the iPS cells were induced from chondrocytes passaged 10 or fewer times after being taken from a live donor. In some embodiments, the iPS cells were induced from chondrocytes passaged 8 or fewer times after being taken from a live donor. In some embodiments, the iPS cells were induced from chondrocytes passaged 6 or fewer times after being taken from a live donor. In some embodiments, the iPS cells were induced from chondrocytes passaged four or fewer times after being taken from a live donor. In some embodiments, the iPS cells were induced from chondrocytes passaged twice or fewer times after being taken from a live donor. In some embodiments, the iPS cells were induced from chondrocytes passaged once after being taken from a live donor. In some embodiments, the iPS cells were induced from chondrocytes that have not been passaged since being taken from a live donor.

In some embodiments, the population of stem cells retain DNA hypo- and hyper-methylation profiles similar to the chondrocytes from which they are derived. In some embodiments, the cells express two or more genes selected from the group consisting of Oct4, Rex-1, SSEA4, Tra1-60 and Tra1-81. In some embodiments, the population of induced pluripotent stem cells is generated by a method comprising directing expression of an Oct3/4 polypeptide, a Sox2 polypeptide, and a Klf4 polypeptide. In some embodiments, directing the expression of Oct 3/4, Sox2, and Klf4, comprises transforming into the chondrocytes one or more expression vectors for directing expression of Oct 3/4, Sox2, and Klf4 polypeptides. In some embodiments, the one or more expression vectors are each independently selected from: retroviral expression vectors, lentiviral expression vectors, adeno-associated viral expression vectors, and adenoviral expression vectors. In some embodiments, at least one of the one or more expression vectors is a lentiviral expression vector.

In some embodiments, the chondrocytes are from a human subject. In some embodiments, the chondrocytes are from an adult human. In some embodiments, the chondrocytes are from a human child or a human adolescent. In some embodiments, the chondrocytes are derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

In some embodiments, the methods for generating a population of pluripotent or multipotent stem cells from a population of chondrocytes further comprises directing expression of a set of polypeptide induction factors. Methods for directing expression of a polypeptide induction factor includes, but is not limited to, introducing expression vectors encoding polypeptide induction factors, introducing exogenous purified induction factor polypeptides into cells, or contacting cells with a non-naturally occurring reagent that induces expression of an endogenous gene encoding a polypeptide induction factor.

In some embodiments, the cells to be induced are cultured for a period of time prior to the induction procedure. Alternatively, in some embodiments, the cells to be induced are used directly in the induction and selection process without a prior culture period.

In some embodiments, different cell culture media is used at different points prior to, during, and after the induction and selection process.

In some embodiments, the selection process includes one or more rounds of positive selection, negative selection, or both.

In some embodiments, the set of induction factor polypeptides comprises one or more of: an Oct3/4 polypeptide, a Sox2 polypeptide, a Klf4 polypeptide, and a c-Myc polypeptide. In some embodiments, the set of induction factor polypeptides does not include a c-Myc polypeptide. In some embodiments, the amino acid sequence of an induction factor polypeptide is a non-naturally occurring amino acid sequence variant of an induction factor polypeptide that is, nevertheless, functionally or structurally homologous to an induction factor polypeptide amino acid sequence, as described herein.

In some embodiments, the set of induction factor polypeptides includes: an Oct3/4 polypeptide, a Sox2 polypeptide, and a Klf4 polypeptide. In some embodiments a single induction factor polypeptide is used for induction, and is selected from Oct 3/4 or Sox2. In some embodiments, the set of induction factor polypeptides includes two induction factor polypeptides, e.g., Oct3/4 and Sox2. In some embodiments, the set of induction factor polypeptides includes three induction factor polypeptides selected from an Oct3/4 polypeptide, a Sox2 polypeptide, a Klf4 polypeptide, and a c-Myc polypeptide.

In some embodiments, the methods disclosed herein further comprise directed expression of an additional induction factor polypeptide. In some embodiments, additional induction factor polypeptides include, but are not limited to Nanog, TERT, LIN28, CYP26A1, GDF3, FoxD3, Zfp42, Dnmt3b, Ecat1, and Tcl1 polypeptides.

In some embodiments, the methods disclosed herein further comprising directing expression of the induction factor polypeptides for a period of at least about 7 days to at least about 40 days, e.g., 8 days, 9 days, 10 days, 11 days, 12 days, 13 days, 14 days, 15 days, 16 days, 17 days, 18 days, 19 days, 20 days, 21 days, 25 days, 30 days, 33 days, 37 days, 40 days, or 45 days.

In some embodiments, the efficiency of inducing pluripotency in cells from a population of chondrocytes is from at least about 0.001% to at least about 0.1% of the total number of parental chondrocyte cells cultured initially, e.g., 0.002%, 0.0034%, 0.004%, 0.005%, 0.0065%, 0.007%, 0.008%, 0.01%, 0.04%, 0.06%, 0.08%, or 0.09%. At times, depending on the age of the donor, the origin of the tissue, or the culture conditions, higher efficiencies may be achieved.

In some embodiments, directed expression of the induction factor polypeptides comprises transforming one or more mammalian expression vectors encoding the induction factor polypeptides into a population of chondrocytes. In some embodiments, genes encoding the induction factor polypeptides are introduced into the cells as exogenous genes. In some embodiments, the exogenous genes are integrated into the genome of a host cell and its progeny. In some embodiments, the exogenous genes persist in an episomal state in the host cell and its progeny.

In some embodiments, the induction factor polypeptides are genetically fused in frame with a transport protein amino acid sequence, e.g., a VP22 polypeptide. In some embodiments, the use of vectors encoding induction factor-VP22 fusion polypeptides increases the functional efficiency of transfected expression vectors in the induction methods described herein.

Examples of suitable mammalian expression vectors include, but are not limited to: recombinant viruses, nucleic acid vectors, such as plasmids, bacterial artificial chromosomes, yeast artificial chromosomes, human artificial chromosomes, transposon vectors, cDNA, cRNA, and PCR product expression cassettes. Examples of suitable promoters for driving expression of IFs include, but are not limited to, retroviral LTR elements; constitutive promoters such as, CMV, CAG, HSV1-TK, SV40, B-actin; PGK, and inducible promoters, such as those containing Tet-operator elements. In some embodiments, one or more of the mammalian expression vectors further comprises a nucleic acid sequence encoding a marker gene that facilitates identification or selection of cells that have been transfected or infected. Examples of marker genes include, but are not limited to, genes encoding fluorescent proteins, e.g., EGFP, DS-Red, monomeric Orange, YFP, and CFP; and antibiotic resistance genes, e.g., the $neo^R$ gene, and the blasticidin resistance gene.

In some embodiments, the methods further comprise selecting and/or screening cells for a number of properties that characterize pluripotent stem cells (e.g., morphological characteristics, gene expression during directed expression of induction factors. In some embodiments, induced cells that meet these screening criteria are subcloned and expanded.

In some embodiments, after directing expression of the induction factor polypeptides, one or more growth factors, such as pigment epithelium-derived factor (PEDF); fibroblast growth factor (FGF)-2; basic FGF (bFGF); platelet-derived growth factor (PDGF), epidermal growth factor (EGF); insulin-like growth factor (IGF); IGF II; or insulin, is included in the culture medium. Other growth factors that can be used to supplement cell culture media include, but are not limited to one or more: Transforming Growth Factor β-1 (TGF β-1), Activin A, Noggin, Brain-derived Neurotrophic Factor (BDNF), Nerve Growth Factor (NGF), Neurotrophin (NT)-1, NT-2, or NT-3. In some embodiments, PEDF is included in the culture medium. In some embodiments, PEDF prevents overgrowth of the induced cell population. In some embodiments the concentration of growth factor(s) is from about 4 ng/ml to about 50 ng/ml, e.g., about 2 ng/ml, 3 ng/ml, 4 ng/ml, 5 ng/ml, 6 ng/ml, 7 ng/ml, 8 ng/ml, 10 ng/ml, 12 ng/ml, 14 ng/ml, 15 ng/ml, 17 ng/ml, 20 ng/ml, 25 ng/ml, 30 ng/ml, 35 ng/ml, 40 ng/ml, 45 ng/ml, or 50 ng/ml. The concentration of growth factors may also be from about 4 ng/ml to about 10 ng/ml; from about 4 ng/ml to about 20 ng/ml; from about 10 ng/ml to about 30 ng/ml; from about 5 ng/ml to about 40 ng/ml; or from about 10 ng/ml to about 50 ng/ml. In other cases, higher concentrations of growth factors may be used, e.g., from about 50 ng/ml to about 200 ng/ml; or from about 75 ng/ml to about 150 ng/ml. In some embodiments, from about 50 ng/ml to about 200 ng/ml of PEDF is added to the post-induction culture medium. In some embodiments, about 100 ng/ml of PEDF is added to the post-induction culture medium.

In some embodiments, morphological characteristics for identifying candidate multipotent or pluripotent cell colonies are selected from: a rounder, smaller cell size relative to surrounding cells and a high nucleus-to-cytoplasm ratio. In some embodiments, the size of the candidate induced cell is from about 5 μm to about 10 μm; from about 5 μm to about 15 μm; from about 5 μm to about 30 μm; from about 10 μm to about 30 μm; or from about 20 μm to about 30 μm. In some embodiments, a high nucleus-to-cytoplasm ratio is from about 1.5:1 to about 10:1, e.g., about 1.5:1; about 2:1; about 3:1; about 4:1; about 5:1; about 7:1; about 8:1; about 9.5:1; or about 10:1. In some embodiments the pluripotent or multipotent cell clones derived from a human or primate display a flattened morphology relative to mouse embryonic stem cells. In some embodiments, another morphological characteristic for identifying induced cell clones is the formation of small monolayer colonies within the space between parental cells (e.g., between chondrocytes).

In some embodiments, the cells in which induction factor expression is directed are plated and cultured directly on tissue culture-grade plastic. Alternatively, cells are plated and cultured on a coated substrate, e.g., a substrate coated with fibronectin, gelatin, Matrigel™ (BD Bioscience), collagen, or laminin. In some cases, untreated petri-dishes may be used. Suitable cell culture vessels include, e.g., 35 mm, 60 mm, 100 mm, and 150 mm cell culture dishes, 6-well cell culture plates, and other size-equivalent cell culture vessels. In some embodiments, the cells are cultured with feeder cells. For example, the cells may be cultured on a layer, or carpet, of MEFs (e.g., irradiated or mitomycin-treated MEFs).

In some embodiments, pluripotent or multipotent cells derived from chondrocytes retain epigenetic memory. In some embodiments, a population of pluripotent or multipotent cells derived from chondrocytes, according to the methods disclosed herein, retain DNA hypo- and hyper-methylation profiles similar to the chondrocytes from which they are derived. In some embodiments, DNA methylation profiles of pluripotent or multipotent cells derived from chondrocytes are different from the DNA methylation profiles of pluripotent or multipotent cells derived from fibroblasts. In some embodiments, the DNA methylation pattern of pluripotent or multipotent cells derived from chondrocytes overlaps more with that of chondrocytes and embryonic stem cells and less with that of pluripotent or multipotent cells derived from fibroblasts.

In some embodiments, markers of chondrogenic precursors and chondrocytes are greater expressed in pluripotent or multipotent cells derived from chondrocytes compared to pluripotent or multipotent cells derived from other cell types. In some embodiments, markers of chondrogenic precursors and chondrocytes include capthesin B, chondrocyte expressed protein-68 (CEP-68), type X collagen, type II collagen, aggrecan, Collagen 9, YKL-39, YKL-40, osteonectin, Sox9, annexin A6, CD44, CD151, type IV collagen, CRTAC1, DSPG3, FoxC1, FoxC2, IBSP/Sialoprotein II, ITM2A, Matrilin-3, Matrilin-4, MIA, OCIL, Otoraplin, Sox5, and URB. In some embodiments, the pluripotent or multipotent stem cells derived from chondrocytes, by the methods disclosed herein, are less than 20% positive for CD73 by FACS analysis. In some embodiments, the pluripotent or multipotent stem cells derived from chondrocytes, by the methods disclosed herein, are less than 15% positive for CD73 by FACS analysis. In some embodiments, the pluripotent or multipotent stem cells derived from chondrocytes, by the methods disclosed herein, are less than 10% positive for CD73 by FACS analysis. In some embodiments, the pluripotent or multipotent stem cells derived from chondrocytes, by the methods disclosed herein, are less than 5% positive for CD73 by FACS analysis. In some embodiments, the pluripotent or multipotent stem cells derived from chondrocytes, by the methods disclosed herein, are positive for expression of endogenous Oct3/4. In some embodiments, the pluripotent or multipotent stem cells derived from chondrocytes, by the methods disclosed herein, lack immunoreactivity to vimentin.

In some embodiments, the pluripotent or multipotent stem cells derived from chondrocytes, by the methods disclosed herein express at least one of the following markers of pluripotent stem cells: ABCG2, cripto, CD9, FoxD3, Connexin43, Connexin45, Oct4, Sox2, Nanog, hTERT, UTF-1, ZFP42, SSEA-3, SSEA-4, Tra1-60, Tra1-81. In some embodiments, other markers for pluripotent stem cells include CD133, CD24, alkaline phosphatase, AFP, BMP-4, Brachyury, CD30, TDGF-1, GATA-4, GCTM-2, Genesis, Germ cell nuclear factor, HNF-4, N-CAM, Pax6, SCF, and telomerase.

In some embodiments, the pluripotent or multipotent stem cells derived from chondrocytes, by the methods disclosed herein, are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic. Methods such as flow cytometry, fluorescence spectroscopy, and Tdt-Utp nick-end labeling (TUNNEL or TUNEL) assay, are used to assess the frequency of apoptosis in a given cell culture.

Generating Chondrocytes from Chondrocyte-Derived Induced Pluripotent Stem Cells

Disclosed herein, in some embodiments, is a method of generating a population of chondrocytes from a population of pluripotent or multipotent stem cells comprising: i) generating a population of pluripotent or multipotent stem cells according to the methods disclosed herein; ii) mechanically dissecting the pluripotent or multipotent stem cell colonies in order to produce cell aggregates; iii) culturing the cell aggregates in a tissue culture-treated vessel until confluency to produce aggregate-derived cells; iv) passaging the aggregate-derived cells in culture at least once to produce chondroprogenitors; and iv) culturing the chondroprogenitors in a three-dimensional culture; wherein the method does not comprise formation of an embryoid body. In some embodiments, the aggregate-derived cells are passaged at least two times. In some embodiments, the aggregate-derived cells are passaged at least three times. In some embodiments, the aggregate-derived cells are passaged at least four times. In some embodiments, the aggregate-derived cells are passaged at least five times. In some embodiments, the aggregate-derived cells are passaged at least six, seven, or eight. In some embodiments, the three-dimensional culture comprises TGF-β3. In some embodiments, the three-dimensional culture comprises BMP2. In some embodiments, the process of producing cell aggregates does not comprise enzymatic digestion of the pluripotent or multipotent stem cells. In some embodiments, the three dimensional culture comprises a three-dimensional matrix. In some embodiments, the three-dimensional matrix comprises collagen, proteoglycan, fibrin, hyaluronic acid, poly-D-lactide, poly-L-lactide, poly-DL-lactide, polyglycolic acid, polylactic acid, hydroxyapatite, calcium phosphate, aterocollagen, fibrin, alginate, agar and/or gelatin. In some embodiments, the three-dimensional matrix comprises collagen. In some embodiments, the collagen is cross-linked. In some embodiments, the collagen is solubilized. In some embodiments, the three-dimensional matrix comprises proteoglycan. In some embodiments, the tissue culture-treated vessel is plastic. In some embodiments, the tissue culture-treated vessel is polystyrene.

In some embodiments, the pluripotent or multipotent stem cells derived from chondrocytes, by the methods disclosed herein, are passaged at least once. In some embodiments, the cells are passaged at least twice. In some embodiments, the cells are passaged at least three times. In some embodiments, the cells are passaged at least four times. In some embodiments, the cells are passaged at least five times. In some embodiments, the cells are passaged at least six times. In some embodiments, the cells are passaged at least seven times. In some embodiments, the cells are passaged at least eight times. In some embodiments, the cells are passaged at least nine times. In some embodiments, the cells are passaged at least ten times. In some embodiments, the cells are passaged at least twelve times. In some embodiments, the cells are passaged at least fifteen times. In some embodiments, the cells are passaged at least twenty times. In some embodiments, the cells are passaged at least twenty five times. In some embodiments, the cells are passaged at least thirty times. In some embodiments, the cells are passaged at least thirty five times.

In some embodiments, disclosed herein is a population of cells, wherein the population of cells has been produced by a process comprising: i) generating a population of pluripotent or multipotent cells from a population of chondrocytes by directing expression of one or more of an Oct3/4, Sox2, Klf4 and c-Myc in the chondrocytes; ii) mechanically dissecting the pluripotent or multipotent cell colonies; iii) passaging the cells in culture at least once to produce chondroprogenitors; and iv) placing the chondroprogenitors in three-dimensional culture. In some embodiments, the population of cells is homogeneous. In some embodiments, the cells are passaged at least four times in order to produce chondroprogenitors.

Three Dimensional Culture

In some embodiments, the pluripotent or multipotent cells derived from chondrocytes by the methods disclosed herein are induced in culture to form chondrogenic precursors. In some embodiments, the pluripotent or multipotent cells derived from chondrocytes by the methods disclosed herein are associated in a three-dimensional format, such as a cell pellet. In some embodiments, the pluripotent or multipotent cells derived from chondrocytes by the methods disclosed herein are associated in a monolayer. In some embodiments, the three dimensional format contributes to the in vitro chondrogenesis of the pluripotent or multipotent cells derived from chondrocytes by the methods disclosed herein. In some embodiments, the pluripotent or multipotent cells derived from chondrocytes by the methods disclosed herein are cultured condensed together, for example, as a packed or pelleted cell mass under gentle centrifugation.

In some embodiments, the chondrocyte-derived pluripotent or multipotent cells are embedded in a matrix gel material. In some embodiments, the matrix gel material comprises one of more of the components: proteoglycans, GAGs, fibers and functional proteins. In some embodiments, the matrix gel material comprises collagen and proteoglycan. Collagen (e.g., Type II collagen, Type III collagen, Type IV collagen, Type V collagen, Type VI collagen, Type VIII collagen, Type IX collagen, Type X collagen, or mixtures thereof) is not particularly limited. In some embodiments, the matrix gel comprises Type I and Type II collagen. In some embodiments, Type II collagen is used.

In some embodiments, the collagen is atelocollagen. In some embodiments, the collagen is low molecular weight collagen hydrolyzed with enzyme. In some embodiments, the collagen is human-derived collagen or collagen derived from rabbits, cattle, horses or mice.

In some embodiments, the matrix gel material comprises at least one proteoglycan. In some embodiments, the proteoglycan is preferably composed of a core protein with pending glycosaminoglycan (GAG) molecules. Suitable GAGs are for instance hyaluronic acid, chondroitin-4-sulfate, chondroitin-6-sulphate, dermatan sulphate, heparin sulphate, heparin sulphate, and keratan sulphate. In some embodiments a GAG molecule is linked to the core protein via a trisaccharide linker (e.g. a GalGalXyl-linker). Exemplary proteoglycans include, but are not limited to, decorin, biglycan, versican and aggrecan. In some embodiments, the proteoglycans are interconnected by hyaluronic acid molecules. In some embodiments, multiple proteoglycans are attached to a single hyaluronic acid backbone.

In some embodiments, the ratio of collagen to proteoglycan is in the range of about 0.3 to about 1.1 relative to about 1 of collagen in weight ratio. In some embodiments, the proteoglycan is in the range of about 0.5 to about 0.7 relative to about 1 of collagen.

In some embodiments, the matrix gel material further comprises one or more functionality-providing proteins such as: glycoproteins such as laminin, entactin, tenascin fibrillin or fibronectin, osteocalcin (Gla protein), osteonectin, and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE), or any combinations thereof. In some embodiments, the total amount of protein is 1-90 wt %, based on the total weight of the gel matrix material.

As culture media for the chondrocyte-derived pluripotent or multipotent cells, it is possible to use the media and additives used for the ordinary culture of the chondrocytes or the mesenchymal cells without limitation. In some embodiments, the culture medium is selected from: RPMI1647, RPMI1640, MEM, BME, 5A, DM120, RITC80-7, F12, L-15, MCDB104 and MCDB107. In some embodiments, the culture medium further comprises serum. In some embodiments, the concentration of the serum is between 1 to 20%. In some embodiments, the concentration of serum is in the range of 5 to 15%. In some embodiments, the concentration of serum is in the range of 5 to 10%. In some embodiments, the serum is bovine serum, fetal calf serum or horse serum. In some embodiments, collagen and proteoglycan are mixed in the medium at an aforementioned predetermined ratio, and are desirably used in the range of the concentration at which they can be gelled and form the three-dimensional structure. In some embodiments, the concentration of collagen is 0.8 to 2.4% by weight and 1.2 to 2.0% by weight, and the concentration of proteoglycan is 0.4 to 1.2% by weight and 0.6 to 1.0% by weight. In some embodiments, the total concentration of collagen and proteoglycan is about 1.2 to 3.6% by weight and preferably about 1.8 to 3.0% by weight.

In some embodiments, chondrocyte-derived pluripotent or multipotent cells are cultured in the presence of chondrogenic growth factors. In some embodiments, chondrogenic growth factors are selected from transforming growth factor-$\beta3$ (TGF-$\beta3$), transforming growth factor-$\beta1$ (TGF-$\beta1$), insulin-like growth factor 1 (IGF-1), and basic fibroblast growth factor (bFGF). In some embodiments, the chondrocyte-derived iPS cells are cultured in the presence of TGF-$\beta3$. In some embodiments, the culture medium also comprises dexamethasone and high glucose. In some embodiments, chondrocyte-specific gene expression is increased in response to TGF-$\beta3$ treatment. In some embodiments, the chondrocyte-specific genes are selected from collagen type 2A1 and aggrecan expression.

In some embodiments, markers of chondrogenic precursors and chondrocytes include capthesin B, chondrocyte expressed protein-68 (CEP-68), type X collagen, type II collagen, aggrecan, Collagen 9, YKL-39, YKL-40, osteonectin, Sox9, annexin A6, CD44, CD151, type IV collagen, CRTAC1, DSPG3, FoxC1, FoxC2, IBSP/Sialoprotein II, ITM2A, Matrilin-3, Matrilin-4, MIA, OCIL, Otoraplin, Sox5, and URB.

In some embodiments, disclosed herein is a population of cells, wherein the population of cells comprises the following characteristics: a) at least 75% of the population of cells is positive for CD73 by FACS analysis; b) at least 75% of the population of cells is positive for CD105 by FACS analysis; c) immunopositive for vimentin; and d) reduced level of Oct3/4 expression. In some embodiments, the population of cells is homogeneous.

In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic. Methods such as flow cytometry, fluorescence spectroscopy, and Tdt-Utp nick-end labeling (TUNNEL or TUNEL) assay, are used to assess the frequency of apoptosis in a given cell culture.

Generating Cardiomyocytes from Chondrocyte-Derived Induced Pluripotent Stem Cells The pluripotent or multipotent cells derived from chondrocytes by the methods disclosed herein may also be differentiated into cardiac muscle cells. In some embodiments, disclosed herein is method of generating a population of cardiomyocytes from a population of pluripotent or multipotent cells comprising: i) generating a population of pluripotent or multipotent cells according to the methods disclosed herein; ii) allowing the population of pluripotent or multipotent stem cells to form embryoid bodies in a culture medium; iii) adding BMP4 to the culture medium; iv) adding BMP4, Activin A, and FGF-$\beta$ for days 1-3 after step iii); v) adding DKK and VEGF for days 3-8 after step iii); and vi) adding DKK, VEGF, and FGF-$\beta$ for days 8-14 after step iii). In some embodiments, on day 0, from about 1 ng/ml to about 10 ng/ml of BMP4 is added to the culture medium. In some embodiments, on day 0, about 5 ng/ml of BMP4 is added to the culture medium. In some embodiments, on day 1, from about 5 ng/ml to about 20 ng/ml of BMP, from about 1 ng/ml to about 10 ng/ml of Activin A, and from about 1 ng/ml to about 10 ng/ml of FGF-beta are added to the culture medium. In some embodiments, on day 1, about 10 ng/ml of BMP4, about 6 ng/ml of Activin A, and about 5 ng/ml of FGF-beta are added to the culture medium. In some embodiments, on day 3, from about 50 ng/ml to about 300 ng/ml of DKK and from 1 ng/ml to about 10 ng/ml of VEGF are added to the culture medium. In some embodiments, on day 3, about 150 ng/ml of DKK and about 5 ng/ml of VEGF are added to the culture medium. In some embodiments, on day 8, from about 50 ng/ml to about 300 ng/ml of DKK, from about 1 ng/ml to about 20 ng/ml of VEGF, and from about 1 ng/ml to about 10 ng/ml of FGF-beta are added to the culture medium. In some embodiments, on day 8, about 150 ng/ml of DKK, about 10 ng/ml of VEGF and about 5 ng/ml of FGF-beta are added to the culture medium.

Uses of Chondrogenic Precursors Derived from Chondrocyte-Derived Induced Pluripotent Stem Cells Disclosed herein, in certain embodiments, are methods of regenerating cartilaginous tissue. In some embodiments, the cartilaginous tissue is auricular cartilage, costal cartilage, articular cartilage, intervertebral cartilage, or tracheal cartilage.

Provided herein, in some embodiments, is a method of treating a bone or cartilage defect, comprising transplanting a population of cells, as produced by the methods disclosed herein (e.g. a population of pluripotent or multipotent cells derived from chondrocytes and/or a population of chondrocytes or chondroprogenitors derived from a population of pluripotent or multipotent cells derived from chondrocytes), to the bone or cartilage defect. In some embodiments, new tissue is produced. In some embodiments, the new tissue integrates with the tissue of the bone or cartilage defect. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin.

Disclosed herein, in some embodiments, is a method of regenerating cartilaginous tissue, comprising transplanting a population of cells, as produced by the methods disclosed herein (e.g. a population of pluripotent or multipotent cells derived from chondrocytes and/or a population of chondrocytes or chondroprogenitors derived from a population of pluripotent or multipotent cells derived from chondrocytes), to a bone or cartilage defect, wherein new cartilaginous tissue is produced. In some embodiments, the population of cells is transplanted into a bone or cartilage defect in a subject in need thereof. In some embodiments, the new cartilaginous tissue integrates with the tissue of the bone or cartilage defect. In some embodiments, the new cartilaginous tissue restores the surface of the cartilage or bone. In some embodiments, the new cartilaginous tissue comprises collagen type II. In some embodiments, the new cartilaginous tissue comprises superficial, intermediate, and deep zones characteristic of normal articular cartilage. In some embodiments, the superficial zone of the new cartilaginous tissue comprises lubricin. In some embodiments, the new cartilaginous tissue does not comprise teratomas, neoplastic cells, evidence of deformation, abnormal architectural features, or other inappropriate cell types.

Cartilage Therapy Material

In some embodiments, the chondrocytes or chondroprogenitors obtained by methods disclosed herein are used for methods of regenerating cartilaginous tissue. In some embodiments, the chondrogenic precursors disclosed herein are placed directly into an area of bone or cartilage defect. In some embodiments, the chondrogenic precursors are placed into an area of bone or cartilage defect with supportive biomaterial. In some embodiments, new cartilaginous tissue products by the chondrocytes obtained by the invention integrates with the tissue of the bone or cartilage defect. In some embodiments, the new cartilaginous tissue restores the surface of the cartilage or bone. In some embodiments, the new cartilaginous tissue comprises collagen type II. In some embodiments, the new cartilaginous tissue comprises superficial, intermediate, and deep zones characteristic of normal articular cartilage. In some embodiments, the superficial zone of the new cartilaginous tissue comprises lubricin. In some embodiments, the new cartilaginous tissue does not comprise teratomas, neoplastic cells, evidence of deformation, abnormal architectural features, or other inappropriate cell types.

Disclosed herein, in some embodiments, are methods of repairing or treating cartilage defects in articular joint surfaces in a subject in need thereof comprising administering to the subject a population of cells, as described herein, at the site of a cartilage defect. In some embodiments, the method also comprises administration to the subject at the site of the cartilage defect an agent or device to block vascular invasion. In some embodiments, a cell-free barrier is placed at the cartilage defect in order to keep the population of cells in place.

Disclosed herein, in some embodiments, is a method of treating a cartilage-related disorder, comprising administration of a population of cells, as described herein (e.g. a population of pluripotent or multipotent cells derived from chondrocytes and/or a population of chondrocytes or chondroprogenitors derived from a population of pluripotent or multipotent cells derived from chondrocytes), to a site of cartilage injury or defect in a subject in need thereof. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a biomaterial and a population of cells as described herein (e.g. a population of pluripotent or multipotent cells derived from chondrocytes and/or a population of chondrocytes or chondroprogenitors derived from a population of pluripotent or multipotent cells derived from chondrocytes). In some embodiments, the chondrogenic precursors are frozen for storage. Freezing can be accomplished under varying conditions and in the presence of various agents or protective compounds. Thus, in some embodiments, freezing is performed in the presence of dimethyl sulfoxide ("DMSO"). DMSO is a well-known protective agent which is inserted into cellular membranes and enables them to be stabilized, which prevents cells from being destroyed. In some embodiments, freezing is performed in the absence of DMSO.

In some embodiments, the chondrogenic precursors are integrated into a biomaterial prior to transplant. Examples of biomaterials into which chondrogenic precursors or their cell mass may be integrated include: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof. In some embodiments, proteoglycans and glycosaminoglycans are sulfated. In some embodiments, the biomaterials is a membrane such as sheet, porous bodies such as sponges, meshes such as knits, textiles, non-woven fabrics, cotton and the like. In some embodiments, the biomaterial is porous material.

In some embodiments, the biomaterial comprises collagen. In some embodiments, the collagen is cross-linked. In some embodiments, the cross-linked collagen is stably fixed to the body of the recipient by a staple or the like.

In some embodiments, the collagen is solubilized to form a collagen solution for admixture with the chondrocytes, and the mixture gelled, if necessary, for use as a cartilage therapy material. In some embodiments, conventional collagen solutions are used. In some embodiments, an enzyme-solubilized collagen solution is used. In some embodiments, a cartilage therapy material is formed by integrating or overlaying a mixture of collagen solution and chondrocytes into or onto a sponge, non-woven fabric or the-like.

In some embodiments, the cartilage therapy material is administered with an agent that prevents or reduces vascularization. Examples of agents that prevent or reduce vascularization include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAEDs) like aspirin and ibuprofen as well as selective cyclooxy-genase-2 inhibitors like celecoxib and rofecoxib steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists, and antibodies to VEGF.

In some embodiments, the cartilage therapy material forms cartilage tissue and induces cartilaginous ossification. Human dermis is an example of such a material which induces cartilaginous ossification. In some embodiments, ossification is also promoted by a growth factor which promotes bone formation, such as bone morphogenetic protein (BMP).

Prior to transplantation of the described cartilage therapy materials, it is preferable to prepare the area that is to be treated. For this purpose, the defect must be prepared to ensure that the implant will take more effectively (particularly as regards its attachment), to reduce the risks of vascularization, etc. Generally, the defect is treated in advance (in order to eliminate all defective cartilage from the area), then it is cleaned. Next, various implantation techniques can be implemented, according to the material being implanted (suspension, matrix, cartilage reconstituted in vitro).

Generally, implantation of the described cartilage therapy materials can be performed by applying various surgical techniques known to the skilled person, and which are experienced in a human clinic, notably implying a stage in which the implant is affixed during surgery, through biodegradable sutures or by the application of bioadhesives. Examples of bioadhesives include, notably, biological glues made of fibrin and/or thrombin, or other biocompatible materials. More particularly, the resorbable biocompatible film is affixed onto the area to be treated, by means of a biological or biocompatible glue. In a preferred variant, the film is positioned on the cartilaginous defect, then the pocket which is thus constituted is filled with cartilage therapy material.

EXAMPLES

Example 1: Transduction of Human Chondrocytes with Lenti-Smart-hOKSM to Establish iPSC Line Derivation Method: pLenti-Smart-hOKSM from InvivoGen, the Genes Oct4, Sox2, Klf4 and c-Myc 293FT-P4 cells were thawed, cultured and passed in DMEM containing 10% FBS, 4.5 g/l glucose, 50 U/ml penicillin, 50 µg/ml streptomycin, 1 mM sodium pyruvate, 4 mM L-glutamine and 0.1 mM non-essential amino acids. Cells were grown at 37° C. in a humidified 5% $CO_2$ incubator. These cells were split every 1-2 days when they reached 70-80% confluency. Cells were not allowed to reach 90% confluency. For subculturing, cells were detached with trypsin/EDTA, and split at a ratio of 1:3-1:10.

Production of Lentiviral Vectors Using HEK 293T Cells

The OKSM plasmid was provided at a concentration of 1 µg/µl in water. 188 µl of sterile water was added to a 12 µl aliquot of pLV-OSKM. This 200 µl solution containing the 12 µg of pLV-OSKM was used to rehydrate the LENTI-Smart.™

LENTI-Smart™ was removed from −20° C. and pre-warmed at room temperature for 10 minutes. The 200 µl solution was added to the LENTI-Smart™ and mixed by gently tapping the bottom of the tube. The mixture was incubated at room temperature for 15 minutes. The total volume was brought up to 1 ml, by adding 800 µl of sterile water and mixed well by gently tapping the bottom of the tube.

HEK 293T cells were trypsinized, and $1 \times 10^7$ HEK 293T cells were added to a T-75 $cm^2$ flask in 12 ml of pre-warmed DMEM containing 10% FBS. The T-75 $cm^2$ flask upright was kept upright. The 1 ml of resuspended LENTI-Smart™ was added gently and directly onto cells and homogenized thoroughly by pipetting up and down several times. The T-75 $cm^2$ flask containing HEK 293T cells and LENTI-Smart™ was incubated horizontally at 37° C., 5% $CO_2$.

After twelve to sixteen hours, the culture medium was discarded from the HEK 293T cells and replaced with 12 ml of pre-warmed fresh medium to further incubate the HEK 293T cells at 37° C., 5% $CO_2$. Note: As a visual control, cells were fused and multinucleated thirty-six to forty-eight hours after transfection, due to the presence of the VSV-G protein. This morphological change was expected and did not affect the production of lentiviral vectors.

Lentiviral supernatant was harvested as follows: supernatants were pooled and collected, and cell debris was removed by centrifugation for 5 minutes at 2000 rpm. Supernatants were filtered using a 0.45 µm filter in order to remove viral capsid debris. The filter was made of PVDF (low protein binding), instead of nitrocellulose.

Hour 0: Transfection
Hour 12: Change medium
Hour 36: 1st harvest
Hour 48: 2nd harvest
Hour 60: 3rd harvest
Transduction Procedure Day 0: Human chondrocyte P2 cells were seeded at appropriate density in a 6-well plate (~5×104). Cells were plated such that cell density was ~25-50% confluent at the time of transduction.

Day 1: Transduction. Medium was removed from the tissue culture plate by aspiration and replaced with 2-3 ml of iPSC reprogram factor lentiviral mixture, as described from above, with an additional 8 µg/ml polybrene. The tissue culture plate was spun in a desktop centrifuge (e.g. Sorvall RT6000) at 1,000×g for 60 min at room temperature to increase transduction efficiency, and the plate was incubated overnight at 37° C.

Day 2: The transduction medium was replaced with 2-3 ml of fresh DMEM medium.

Day 3-4: Medium was replaced. Some cell death was observed due to c-Myc induced apoptosis.

Day 4: HS27 MEF feeder cells and gelatin-coated plates. ($2.4 \times 10^6$ cells/plate) were prepared, in incomplete ES medium Day 5: Cells were trypsinized and plated out on 10 cm gelatin-coated plates, one 6 well to two 10 cm plates, and cultured with hESC media, one set with PEDF (Peprotech, 100 ng/ml) without FGFb, the other set with FGFb (16 ng/ml, R&D) only, both with 1 mM valproic acid.

Medium was changed every day and the plates were observed under the microscope to identify ES like colonies.

Incomplete Human iPSC serum-free medium (500 ml, filtered with 0.22 µm filter):

1. Knockout serum replacement 100 ml 20% final
2. Penicillin/Streptomycin 5 ml 100 U and 100 µg per ml final
3. L-glutamine (200 mM) 5 ml 2 mM final
4. Non-essential Amino 88 Acids 5 ml 100 µM final
5. 2-mercaptoethanol (55 mM) 0.9 ml 100 µM final
6. DMEM/F12 fill to 500 ml After the colonies were selected, the colonies were maintained and expanded in regular human ES medium for further experiments.

Example 2: Differentiation of iPSC Cells into Chondroprogenitors

Chondroprogenitors were differentiated from iPSC or a human embryonic stem cell (hESC) (WAO9, Wicell) by culturing in DMEM/F12 containing 10% FBS. Chondrogenic differentiation of chondroprogenitors were done in pellet culture by spinning down $5 \times 10^5$ cells to form a pellet and cultured in chondrogenic media (Lonza) containing TGFβ3 with or without BMP4. After 2 weeks, type II collagen expression in these pellets was verified with qPCR.

Figure 1:
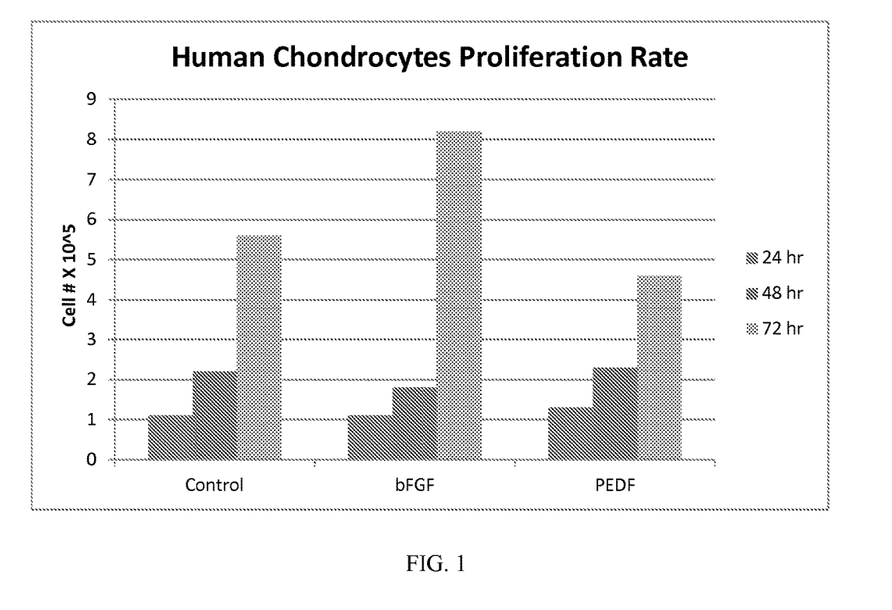
FIG. 1 exemplifies proliferation rate of human chondrocytes transfected with Lentismart OKSM in the presence of FGF-β (10 ng/ml) or PEDF (100 ng/ml). Control indicates the culture medium, (DMEM/F12 with 10% FBS).
Figure 2:
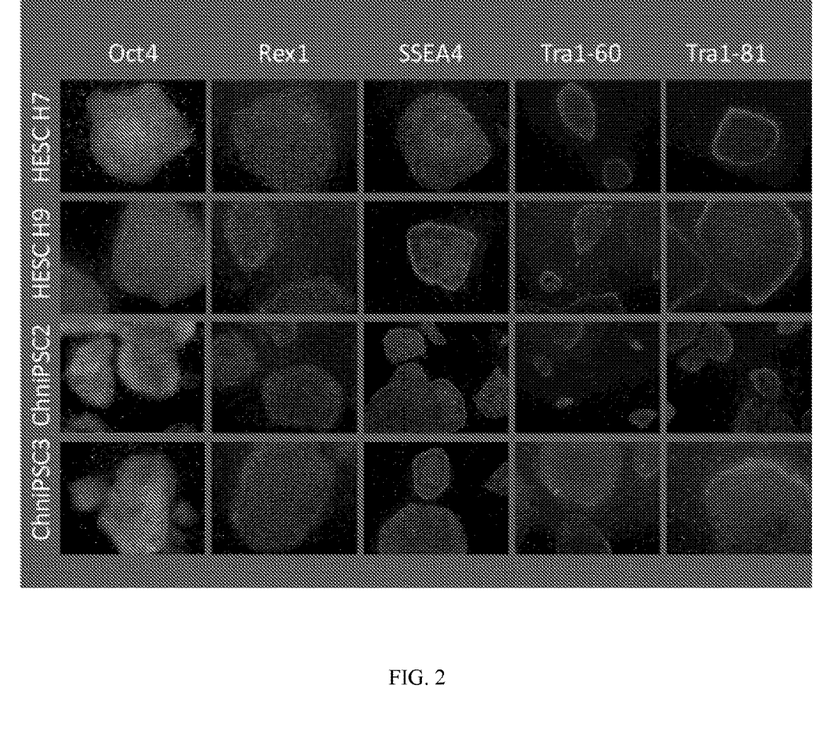
FIG. 2 exemplifies iPSCs derived from human chondrocytes as expressing pluripotent stem cell markers. After transforming human articular chondrocytes with lentiviral expression vectors for Oct4, Sox2, Klf4, and c-Myc, two cell lines (ChniPSC2 and ChniPSC3) morphologically resembling human embryonic stem cells were expanded. Human embryonic stem cell lines H7 and H9 were used as positive controls. Immunocytochemistry results indicated that both iPSC lines, ChniPSC2 and ChniPSC3, were positive for Oct4, Rex-1, SSEA4, Tra1-60, and Tra1-81 expression. The expression level of the markers and the morphology of iPSC are indistinguishable from the H7 and H9 human embryonic stem cell lines.
Figure 3:
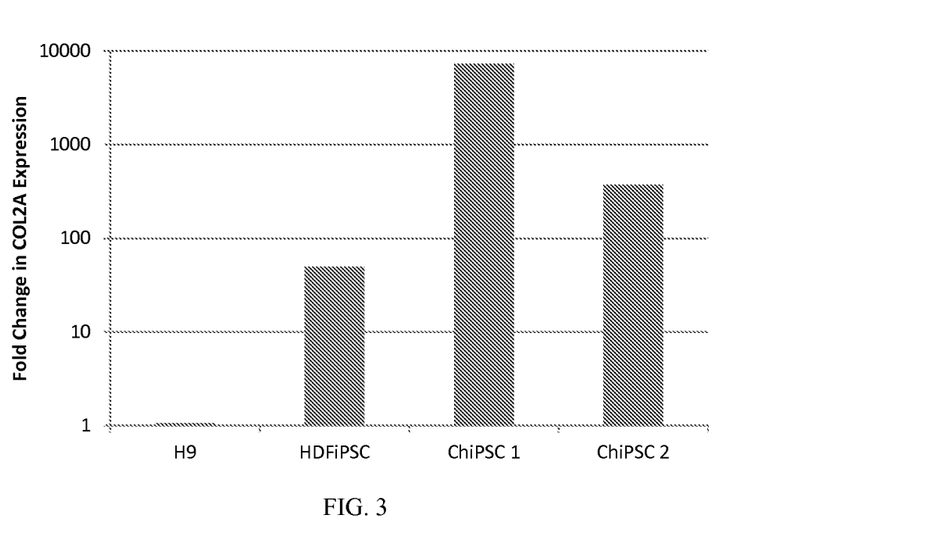
FIG. 3 exemplifies the chondrogenic potential of iPSC cell lines (ChIPSC and ChiPSC 2 derived from chondrocytes; HDFiPSC derived from human dermal fibroblasts) in pellet culture as indicated by type II collagen mRNA expression, where H9 exemplifies human embryonic stem cell line H9 becoming chondrogenic in pellet culture. The iPS cell lines derived from chondrocytes expressed far greater type II collagen mRNA (y axis is a log scale).
Figure 4:
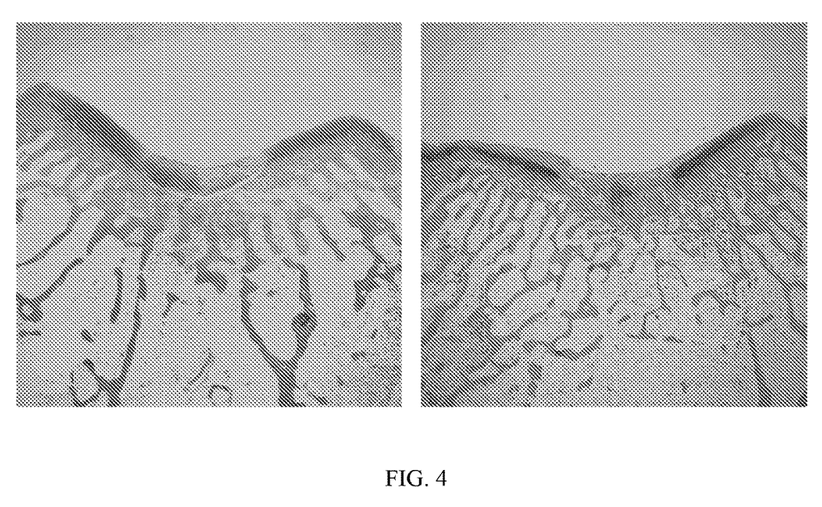
FIG. 4 exemplifies chondroprogenitors differentiated from both chondrocyte-derived iPSC cells lines being able to fill cartilage defects with regenerated tissue at 8 weeks after in vivo implantation in rabbit knees. The defects in the joint tissue became filled with tissue which stained positive for glycosaminoglycans (by Safranin O stain).

A partial thickness defect (2 mm) was surgically created in trochlear surfaces of rabbit knees. Chondroprogenitors differentiated from chondrocyte-derived iPSC cell lines were transplanted into this defect. After 8 weeks, tissue was harvested, fixed with zinc-formalin, embedded in paraffin, sectioned and stained with Safranin-O/Fast Green. The defects in the rabbit knees became filled with Safranin O staining positive extracellular matrix (FIG. 4).

Example 3: Repairing Cartilage Defects in Explants from Adult Human Arthritic Joints by Transplantation Osteochondral specimens are surgically resected from the joints of adult arthritic human patients undergoing total knee replacement. Six-mm diameter cylindrical plugs are cored out. A surgical curette is used to make partial-thickness defects approximately 2 mm in size in the articular surface. The defects are filled with chondrogenic precursors produced from chondrocyte-derived iPS cells, which are aggregated under the following mechanical pressures: $5 \times 10^5$ cells centrifuged in 15-ml conical tubes at 150 g for 5 min in DMEM/F12 supplemented with 10% FBS and incubated overnight in the presence or absence of TGFβ3. After 4 weeks, explants are fixed, paraffin-embedded, sectioned, and stained with Safranin O for immunohistochemical examination.

Example 4: Repairing Cartilage Defects in Adult Human Arthritic Joints by Intraarticular Injection A patient with osteoarthritis of the knee is injected in an arthritic knee joint with cells according to the invention (e.g., a population of pluripotent or multipotent cells derived from chondrocytes and/or a population of chondrocytes or chondroprogenitors derived from a population of pluripotent or multipotent cells derived from chondrocytes) suspended in alginate. Maintenance injections are given as needed.

Example 5: Repairing Cartilage Defects in Adult Human Arthritic Joints by Surgical Implantation A patient with osteoarthritis of the knee or with a cartilage and/or a bone defect is treated by surgically implanting cells according to the invention (e.g., a population of pluripotent or multipotent cells derived from chondrocytes and/or a population of chondrocytes or chondroprogenitors derived from a population of pluripotent or multipotent cells derived from chondrocytes) and matrix.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of generating a population of isolated mammalian cells expressing Oct4, Rex1, SSEA4, Tra1-60, and Tra1-81 from a population of chondrocytes, comprising:
    a) introducing at least one nucleic acid encoding an Oct3/4 polypeptide, a Sox2 polypeptide, and a Klf4 polypeptide, into a population of chondrocytes; and
    b) culturing the chondrocytes of step a) in the presence of pigment epithelium-derived factor (PEDF) such that a population of isolated mammalian cells expressing Oct4, Rex1, SSEA4, Tra1-60, and Tra1-81 are obtained.

2. The method of claim 1, wherein the chondrocytes are from an adult human.

3. The method of claim 1, wherein PEDF decreases the proliferation rate of the chondrocytes.

4. The method of claim 1, wherein PEDF is present in the culture at a concentration of about 50 ng/mL to about 200 ng/mL.

5. The method of claim 1, wherein PEDF is present in the culture at a concentration of about 75 ng/mL to about 150 ng/mL.

6. The method of claim 1, wherein PEDF is present in the culture at a concentration of about 100 ng/mL.

7. The method of claim 1, wherein the cells expressing Oct4, Rex1, SSEA4, Tra1-60, and Tra1-81 have a rounder, smaller cell size relative to the chondrocytes.

8. The method of claim 1, wherein the cells expressing Oct4, Rex1, SSEA4, Tra1-60, and Tra1-81 have a higher nucleus-to-cytoplasm ratio relative to the chondrocytes.

* * * * *

UNITED STATES PATENT AND TRADEMARK OFFICE
CERTIFICATE OF CORRECTION

PATENT NO. : 9,914,911 B2  
APPLICATION NO. : 14/438581  
DATED : March 13, 2018  
INVENTOR(S) : Darryl D. D'Lima et al.

Page 1 of 1

It is certified that error appears in the above-identified patent and that said Letters Patent is hereby corrected as shown below:

On the Title Page

Item [12], Column 1, Line 2, please delete "d'Lima et al." and replace with "D'Lima et al."

Item [72], Column 1, Line 6, please delete "d'Lima" and replace with "D'Lima"

Signed and Sealed this
Tenth Day of July, 2018

Andrei Iancu
*Director of the United States Patent and Trademark Office*